US010441392B2

(12) United States Patent
Geier (10) Patent No.: US 10,441,392 B2
(45) Date of Patent: Oct. 15, 2019

(54) IMPLANT ANALOGS HAVING TRANSVERSE COMPONENT

(71) Applicant: Zfx GmbH, Dachau (DE)

(72) Inventor: Andreas Geier, Gargazon (IT)

(73) Assignee: Zfx GmbH, Dachau (DE)

( * ) Notice: Subject to any disclaimer, the term of this patent is extended or adjusted under 35 U.S.C. 154(b) by 0 days.

(21) Appl. No.: 14/859,623

(22) Filed: Sep. 21, 2015

(65) Prior Publication Data
US 2016/0089222 A1 Mar. 31, 2016

Related U.S. Application Data

(60) Provisional application No. 62/056,306, filed on Sep. 26, 2014.

(51) Int. Cl.
*A61C 13/34* (2006.01)
*A61C 8/00* (2006.01)

(52) U.S. Cl.
CPC ............ *A61C 13/34* (2013.01); *A61C 8/0001* (2013.01)

(58) Field of Classification Search
CPC .............................. A61C 8/0001; A61C 13/34
See application file for complete search history.

(56) References Cited

U.S. PATENT DOCUMENTS

| 4,840,565 | A | * | 6/1989 | Poveromo | A61C 9/002 433/74 |
| 4,846,684 | A | * | 7/1989 | Oestreich | G09B 23/283 433/213 |
| 4,902,232 | A | * | 2/1990 | Neustadter | G09B 23/283 434/263 |
| 4,969,820 | A | * | 11/1990 | Oestreich | G09B 23/283 433/213 |
| 5,030,102 | A | * | 7/1991 | Lang | G09B 23/283 433/193 |
| 5,222,891 | A | * | 6/1993 | Poveromo | A61C 9/002 433/74 |
| 6,257,895 | B1 | * | 7/2001 | Oestreich | G09B 23/283 434/263 |
| 6,719,562 | B1 | * | 4/2004 | Oestreich | G09B 23/283 433/213 |

(Continued)

FOREIGN PATENT DOCUMENTS

| CN | 107278143 A | 10/2017 |
| DE | 202014005802 U1 | 8/2014 |

(Continued)

OTHER PUBLICATIONS

"International Application Serial No. PCT/EP2015/071877, International Search Report dated Dec. 7, 2015", 5 pgs.

(Continued)

*Primary Examiner* — Cris L. Rodriguez
*Assistant Examiner* — Hao D Mai
(74) *Attorney, Agent, or Firm* — Schwegman Lundberg & Woessner, P.A.

(57) ABSTRACT

Various implant analogs, model, and base designs are disclosed herein. In one example, an implant analog can include a main body and a second component. The main body can have an axis of symmetry and a passage therein. The second component can be received in the passage so as to extend substantially transverse to the axis of symmetry.

16 Claims, 11 Drawing Sheets

(56) References Cited

U.S. PATENT DOCUMENTS

| | | | |
|---|---|---|---|
| 9,375,298 B2* | 6/2016 | Boronkay | A61C 9/002 |
| 9,501,954 B2* | 11/2016 | Higashimura | G09B 23/283 |
| 9,763,758 B2* | 9/2017 | Kopelman | A61C 13/0004 |
| 2003/0044753 A1 | 3/2003 | Marotta | |
| 2006/0078847 A1* | 4/2006 | Kwan | A61C 8/0001 |
| | | | 433/174 |
| 2007/0224576 A1* | 9/2007 | Ihde | A61C 8/0001 |
| | | | 433/173 |
| 2008/0124676 A1* | 5/2008 | Marotta | A61C 1/084 |
| | | | 433/174 |
| 2008/0171305 A1 | 7/2008 | Sonenfeld et al. | |
| 2009/0081613 A1* | 3/2009 | Ihde | A61C 8/0001 |
| | | | 433/173 |
| 2009/0104585 A1* | 4/2009 | Diangelo | A61C 8/0001 |
| | | | 433/223 |
| 2009/0130630 A1* | 5/2009 | Suttin | A61C 1/084 |
| | | | 433/174 |
| 2009/0325125 A1* | 12/2009 | DiAngelo | A61C 8/0001 |
| | | | 433/173 |
| 2010/0021859 A1 | 1/2010 | Kopelman | |
| 2012/0088208 A1* | 4/2012 | Schulter | A61C 8/0001 |
| | | | 433/173 |
| 2012/0135373 A1* | 5/2012 | Cheng | A61C 1/084 |
| | | | 433/75 |
| 2013/0269165 A1* | 10/2013 | Marotta | A61B 19/50 |
| | | | 29/428 |
| 2013/0289950 A1* | 10/2013 | Kopelman | A61C 13/0004 |
| | | | 703/1 |
| 2013/0330689 A1* | 12/2013 | Woldegergis | A61C 8/0001 |
| | | | 433/213 |
| 2014/0154638 A1 | 6/2014 | Kats | |
| 2014/0186796 A1* | 7/2014 | Suttin | A61C 8/0001 |
| | | | 433/172 |
| 2014/0342306 A1* | 11/2014 | Lerner | A61C 13/083 |
| | | | 433/34 |

FOREIGN PATENT DOCUMENTS

| | | |
|---|---|---|
| DE | 102013104352 A1 | 9/2014 |
| WO | WO-2016046267 A1 | 3/2016 |

OTHER PUBLICATIONS

"International Application Serial No. PCT/EP2015/071877, Written Opinion dated Dec. 7, 2015", 7 pgs.

"International Application Serial No. PCT/EP2015/071877, International Preliminary Report on Patentability dated Apr. 6, 2017", 9 pgs.

"European Application Serial No. 15766877.3, Response filed Nov. 15, 2017 to Communication pursuant to Rules 161(1) and 162 EPC dated May 8, 2017", 22 pgs.

"Chinese Application Serial No. 201580057653.6, Office Action dated Jan. 25, 2019", (W/ English Translation), 12 pgs.

"Chinese Application Serial No. 201580057653.6, Response filed Apr. 26, 2019 to Office Action dated Jan. 25, 2019", w/ English claims, 14 pgs.

* cited by examiner

IMPLANT ANALOGS HAVING TRANSVERSE COMPONENT

CLAIM OF PRIORITY

This application claims the benefit of U.S. Provisional Patent Application Ser. No. 62/056,306, filed on Sep. 26, 2014, the benefit of priority of which is claimed hereby, and which is incorporated by reference herein in its entirety.

TECHNICAL FIELD

This document pertains generally to implant analogs used in the production of custom-made prosthetic structures on dental implants, and more particularly, to implant analogs having a transverse component.

BACKGROUND

In the field of dental implantology, before surgical placement of implants in a patient's mouth, an assembly of a prosthetic device and implants is custom fit to the patient's mouth. Custom fitting involves taking an impression of the patient's mouth in a known fashion and reproducing a facsimile of the patient's mandible and/or maxilla in the form of a model. Models may be comprised of gypsum or other materials. The models are mounted on a base. The custom fitting of the prosthetic device proceeds with the use of an implant analog that is placed in the model in a position analogous to the desired ultimate position into which the implant itself will be surgically implanted in the patient's mandible or maxilla. The prosthetic device can be a crown, bridge or a more complete set of prosthetic teeth.

The custom fitting procedure must be able to accommodate the great variability of the shape of the mandible or maxilla from patient to patient. Some fittings may require the implant analogs to be placed in the model. In some cases, the implant analogs may be disposed at an angle that is not vertical to the base. Where multiple implants will be used to support a prosthetic device, the angles at which each implant is placed in the model can vary. During the fitting procedure it is possible for one implant analog to properly engage the prosthetic device while a separate implant analog fails to engage properly or may even break. In the event adjustments are needed, delay, inaccuracy and other problems may arise where the prosthetic device and implant analogs must be removed from the top of the model, that is, from the side of the model engaging the prosthetic device. If only a single implant analog needs to be adjusted, it is problematic to remove the entire bridge and other implants. Where the angle of implant analogs vary, it is also problematic to remove them. If an individual analog is damaged it may be difficult to remove it without the time and consequent expense of removing the entire assembly.

Implant analogs represent the implant present in the mouth of the patient. If abutments are already mounted on the implant, the implant analogs can also represent the abutments. Likewise, implant analogs can also represent parts of the abutment and of the implant in some implant systems.

Implant analogs used to make master casts for subsequent production of custom-made prosthodontic superstructure in exact agreement with the implants in the jawbones are themselves known. The implant analog is included in the master cast, with the future prosthodontic superstructure being attached to the head of the implant analog and, after the implant superstructure has been produced, transferred to the implant inserted in the mouth of the patient.

SUMMARY

To better illustrate the implant analogs, models and related methods disclosed herein, a non-limiting list of examples is provided here:

Implant analogs can be difficult to position, affix, and adjust within the model. The present inventor has recognized that the process of positioning, affixing, an/or adjusting the implant analog within the model can be improved by providing an implant analog with a transverse component such as a pin. The main body of the implant analog can be provided with a bore that allows for passage of the transverse component therethrough. The model can also be provided with a transverse passage that receives the transverse component. The transverse component can be inserted into the transverse passage of the model can through the bore to affix the implant analog within the model. Additionally, as the transverse passages within the model has a fixed relationship relative to the implant analogs and other portions of the model, the arrangement allows for alignment of the implant analog in a desired position in addition to affixation. In some instances, various tools can be used from implantation and/or removal of the implant analog including the main body and/or the transverse component. In some cases the transverse passage may allow for ease of removal or adjustment of the transverse component, allowing the main body of the implant analog to be removed from the model and/or adjusted as necessary. In some instances, the model can be formed by additive or subtractive methods. Additionally, the implant analogs and model can be utilized in conjunction with one or more bases as disclosed herein.

Various implant analogs, model, and base designs are disclosed herein. In one example, an implant analog can include a main body and a second component. The main body can have an axis of symmetry and a passage therein. The second component can be received in the passage so as to extend substantially transverse to the axis of symmetry.

In another example, a system for simulating a mouth of a patient, can include at least one implant analog and a model. The implant analog can have a main body and a component extending substantially transverse to the main body. The model can have at least one primary passage and at least one passage extending substantially transverse to the primary passage, wherein the model is configured for the primary passage to receive the main body and the transverse passage to receive the component.

In yet another example, a method for affixing an implant analog to a model, can include, providing implant analog having a main body with a receptacle therein, passing the main body through a first passage in the model, and passing a component through a second passage in the model and into the receptacle in the main body, the second passage intersecting and substantially transverse to the first passage.

This Summary is intended to provide non-limiting examples of the present subject matter—it is not intended to provide an exclusive or exhaustive explanation. The Detailed Description below is included to provide further information about the present prosthetic match holder, reference member, and methods.

BRIEF DESCRIPTION OF THE DRAWINGS

In the drawings, which are not necessarily drawn to scale, like numerals can be used to describe similar elements throughout the several views. The drawings illustrate generally, by way of example, but not by way of limitation, various embodiments discussed in the present document.

DETAILED DESCRIPTION

The present disclosure describes a various embodiments of implant analogs as well as models adapted to receive the implant analogs therein. As discussed, the implant analogs can include a transverse component that extends through a main body of the implant analog. The transverse component can be used to aid in positioning, affixing, adjusting, and removing the implant analog within the model. Various examples of models are disclosed that can adapted to receive the implant analog including the transverse component. Each of the models can be configured to allow for positioning, affixing, adjusting, and removing the implant analog within the model. In further examples, a base and pins are disclosed that can be utilized with the model(s) and implant analogs.

Figure 1A:
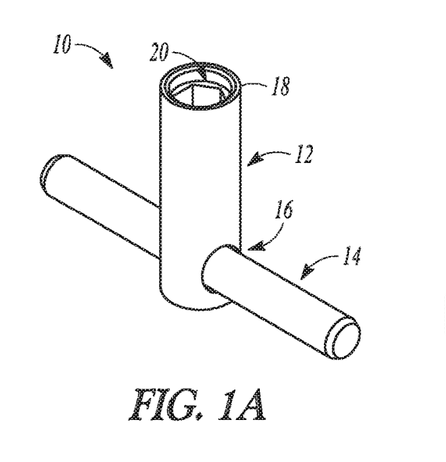
FIG. 1A is a perspective view of an implant analog having a main body and a transverse component, in accordance with an example of the present disclosure.
Figure 1B:
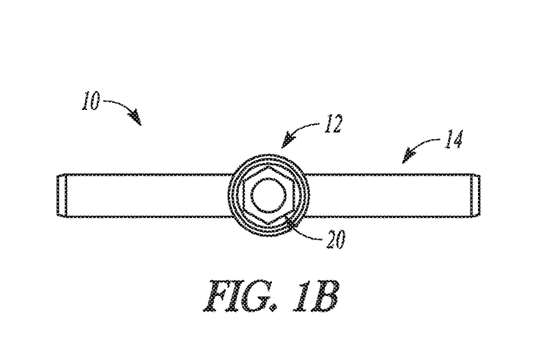
FIG. 1B is a top view of the implant analogy, in accordance with an example of the present disclosure.
Figure 1C:
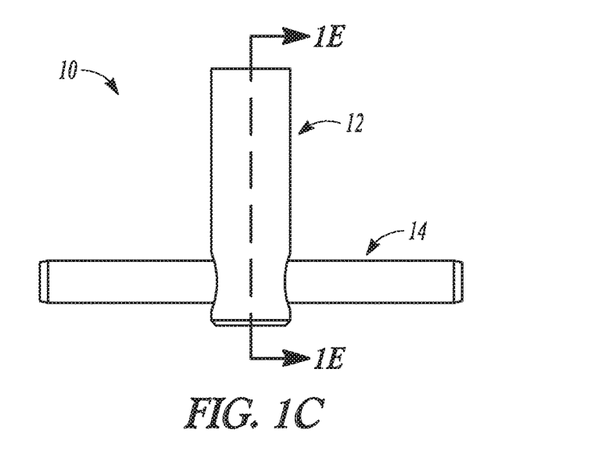
FIG. 1C is a plan view of a first side of the implant analogy, in accordance with an example of the present disclosure.
Figure 1D:
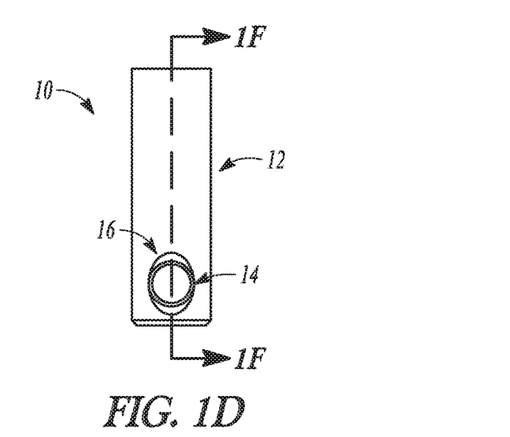
FIG. 1D is a plan view of a second side of the implant analogy, in accordance with an example of the present disclosure.
Figure 1E:
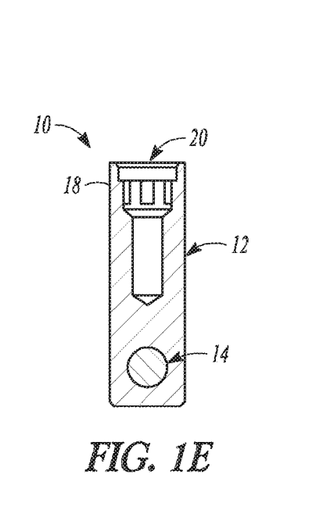
FIG. 1E is a cross-sectional view of the implant analog taken along line 1E-1E of FIG. 1C.
Figure 1F:
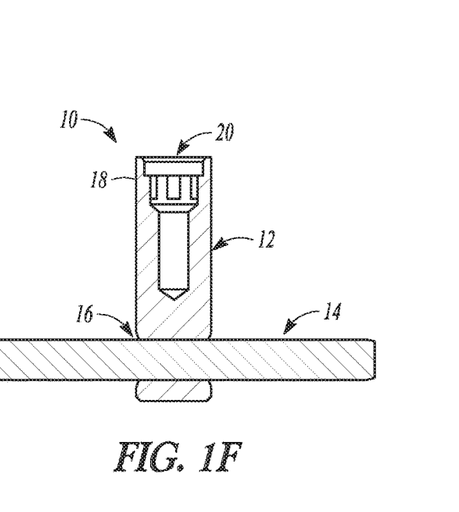
FIG. 1F is a second cross-sectional view of the implant analog taken along line 1F-1F of FIG. 1D.

FIG. 1A is a perspective view of an implant analog 10. FIGS. 1B, 1C, and 1D provide plan views of the implant analog 10 from the top, a first side, and a second side, respectively. FIGS. 1E and 1F are cross-sections of the implant analog taken along lines indicated in FIGS. 1C and 1D. The implant analog 10 can include a main body 12 and a transverse component 14. The main body 12 can include a transverse bore 16 and a coronal end 18. The coronal end 18 can have an attachment feature 20.

It should be noted that the implant analogs described in the following are equally suitable for single-tooth implants and for bridge implants, as well as for telescope crown and bridge work or zirconia-based restorations in the dental laboratory. With the appropriate working surface, they can be used for any implant system.

As illustrated in FIGS. 1A-1F, the transverse component 14 can comprise a pin that passes through the main body 12. Main body 12 can have a substantially cylindrical pin-like shape as illustrated in FIGS. 1A-1F. In other examples, not specifically illustrated, the main body 12 and transverse component 14 can have other non-cylindrical shapes.

In particular, the main body 12 is adapted with the transverse bore 16 extending therethrough (FIGS. 1A, 1D, and 1F). The transverse bore 16 is adapted to receive the transverse component 14 therein. As illustrated in FIGS. 1D and 1F, the transverse bore 16 can include a tapered outer portion to ease reception of the transverse component 14 therein.

The coronal end 18 of the main body 12 can be spaced from the transverse bore 16 and transverse component 14. The coronal end 18 can be adapted with the attachment feature 20. In the embodiment of FIGS. 1A-1F, the attachment feature 20 can comprise a counter bore having an attachment pattern (e.g., a hexagonal attachment pattern). It should be recognized that a plurality of different types of attachment features are anticipated including male type attachments (e.g., ball). It is also should be recognized that in some instances the main body can include a head that simulates an abutment or similar dental attachment feature. The head can be integral with (i.e. part of) the main body or can be a separate component.

Figure 2:
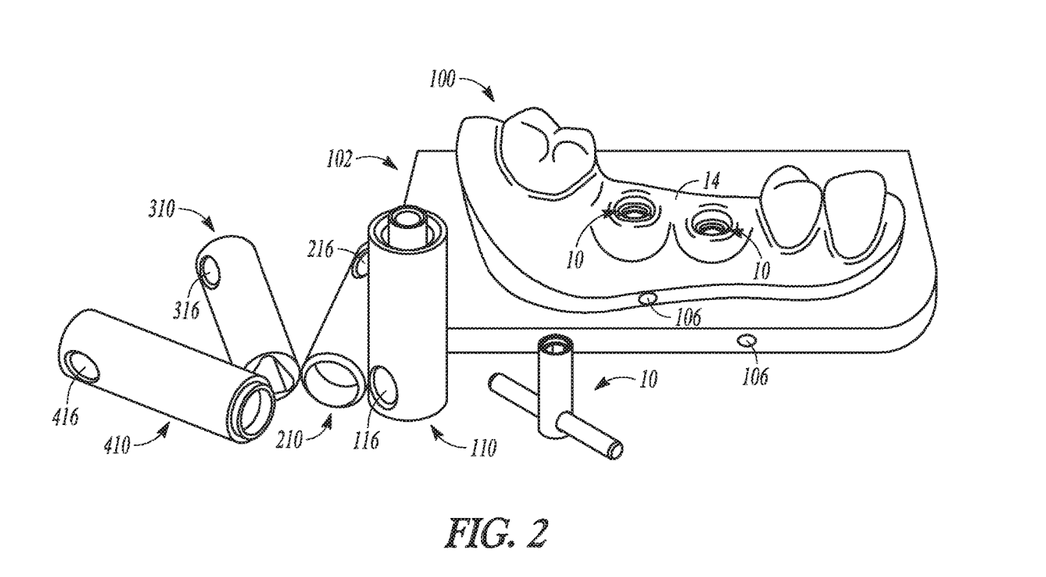
FIG. 2 is a perspective view of a model and various implant analogs, in accordance with an example of the present disclosure.

FIG. 2 illustrates a portion of a model 100 and various examples of implant analogs 10, 110, 210, 310, and 410. The model 100, sometimes referred to as a cast or model, can be used to simulate the anatomy of the patient. In particular, a negative impression of the patent's jaw can be produced with an impression tray filled with impression compound, using system-specific impression posts as carriers. It is removed from the jaw and filled with a casting material that, after hardening, represents an accurate model of the patient's jaw. In place of implants, etc., the implant analog(s) are inserted into the model. The implant analogs are placed in the model with its working surface oriented and positioned by exact analogy with the implant in the patient's jaw.

The model 100 can be formed with or disposed on a base 102. The model 100 can be configured to receive the implant analogs 10 therein. As illustrated in FIG. 2, two implant analogs 10 are inserted in the model and have coronal ends exposed to a working surface 104 of the model 100. The working surface 104 is adapted to receive components that simulate abutments or other dental implant components. To accommodate the implant analogs 10, the model 100 can be provided with one or more primary bores (illustrated as receiving implant analogs 10) and one or more transverse bores 106. In the example illustrated in FIG. 2, each transverse bore 106 is open to at least one side of the model 100 and communicates with a respective primary bore (or the implant analog filling the primary bore). In other examples, the transverse bore 106 may not open to a side surface of the model 100.

FIG. 2 illustrates additional embodiments of the implant analogs 110, 210, 310, and 410. These examples are illustrated having varying sizes and varying attachment features (e.g., lobed female, male, etc.). The appropriate implant analog will be selected based upon various factors including the size, shape, abutment type desired, dentist preference, etc. For simplicity, the transverse components have been removed from the implant analogs 110, 210, 310, and 410. However, transverse bores 116, 216, 316, and 416 are illustrated as extending through each of the implant analogs 110, 210, 310, and 410, respectively.

Figure 3A:
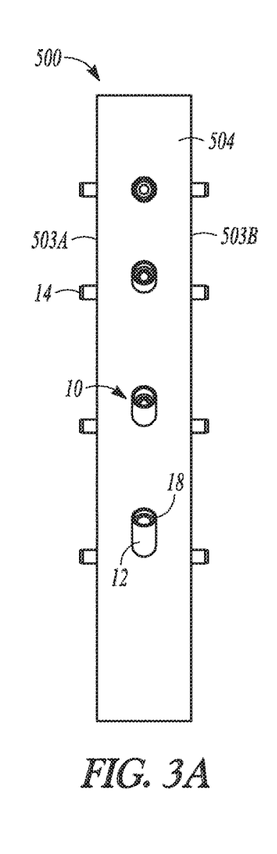
FIG. 3A is a top view of a model and a plurality of implant analogs, in accordance with an example of the present disclosure.
Figure 3B:
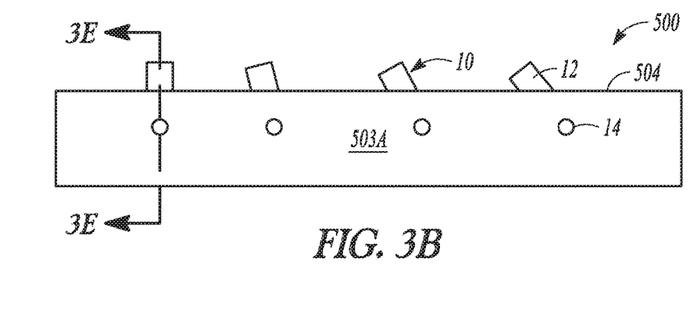
FIG. 3B is a first side view of the model and the plurality of implant analogs, in accordance with an example of the present disclosure.
Figure 3C:
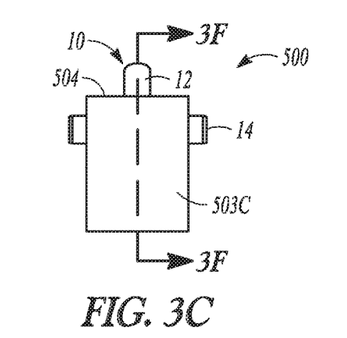
FIG. 3C is second end view of the model and the plurality of implant analogs, in accordance with an example of the present disclosure.
Figure 3D:
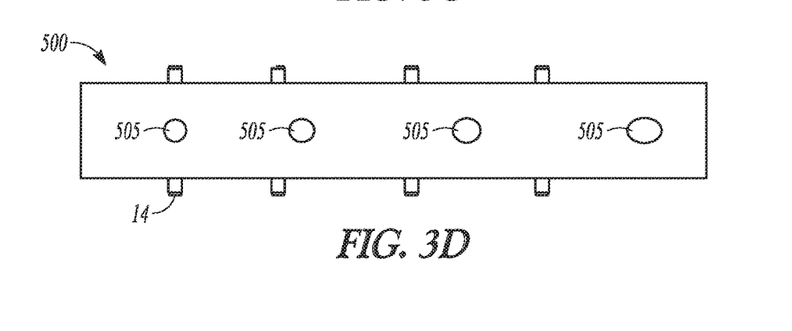
FIG. 3D is a bottom view of the model and the plurality of implant analogs, in accordance with an example of the present disclosure.
Figure 3E:
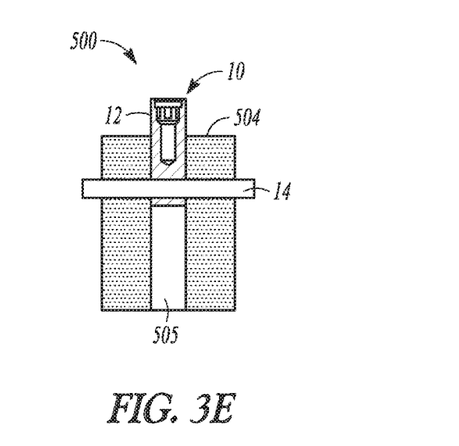
FIG. 3E is a cross-sectional view of the model taken through one of the implant analogs, the cross-section taken along line 3E-3E of FIG. 3B.
Figure 3F:
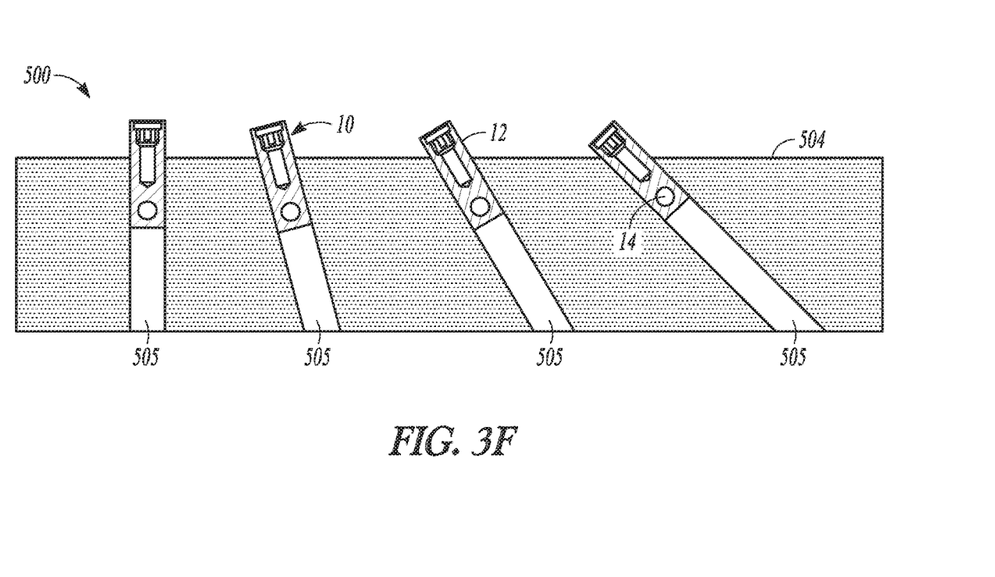
FIG. 3F is a second cross-sectional view of the model taken through one of the implant analogs, the cross-section taken along line 3F-3F of FIG. 3C.

FIGS. 3A-3F illustrate a highly schematic example of a model 500. Although described in reference to a model, in some instances, a bridge or separate component that can be removed from inserted in a model can also be used in a manner similar to as described as follows. FIGS. 3A, 3B, 3C, and 3D provide plan views of the model 500 from various sides including the top, first side, second side, and bottom. FIGS. 3E and 3F are cross-sections of the implant analog taken along lines indicated in FIGS. 3B and 3C. As illustrated in FIGS. 3D-3F, the model 500 can include a plurality of primary bores 505 therein. The model 500 can additionally include a plurality of transverse bores (each illustrated receiving the transverse component 14).

As illustrated in FIGS. 3A-3F the model 500 can receive one or more implant analogs 10 therein. As shown in FIG. 3A, the main body 12 of each implant analog 10 can extend from the primary bore to be positioned at least partially outside a working surface 504 of the model 500. This arrangement can allow the coronal portion 20 to receive a component that simulates an abutment or other type of dental implant feature. Similarly, the transverse component 14 can extend from transverse bore to be positioned at least partially outside side surfaces 503A and 503B.

FIGS. 3B and 3C illustrate the model 500 from sides 503B and 503C, respectively. FIG. 3D illustrates the bottom base interfacing portion of the model 500. Attachment features that would allow the model 500 to mount to a base (not shown) are not illustrated in the highly schematic depiction of FIG. 3D. FIG. 3D and FIG. 3F illustrate that the primary bores 505 can be angled relative to the working surface 504 (FIGS. 3A, 3B, 3C, 3E, and 3F) to varying degrees, and need not be substantially transverse thereto. Thus, the primary bores 505 may be angled relative to one another in some instances. The nature of the angle can be determined based upon various factors including size constraints of the component installed along the working surface of the model.

As discussed, the model 500 can be configured to receive the implant analogs 10 therein. The main body 12 of each implant analog 10 is affixed to the model 500 by the transverse component 14. The configuration of the model 500 and the implant analogs 10 can allow the process of positioning, affixing, and/or adjusting the implant analogs 10 within the model 500 to be simplified. In particular, the transverse component 14 can simply be grasped, pushed, and/or pulled with or without tools to remove the transverse component 14 from the model 500. This then allows the main body 12 to be adjusted or removed from the model 500 as necessary. Additionally, as each of the transverse passages within the model 500 has a fixed relationship relative to the implant analogs and other portions of the model 500 (e.g., working surface 504), the arrangement allows for alignment of the implant analog in a desired position in addition to affixation.

Figure 4A:
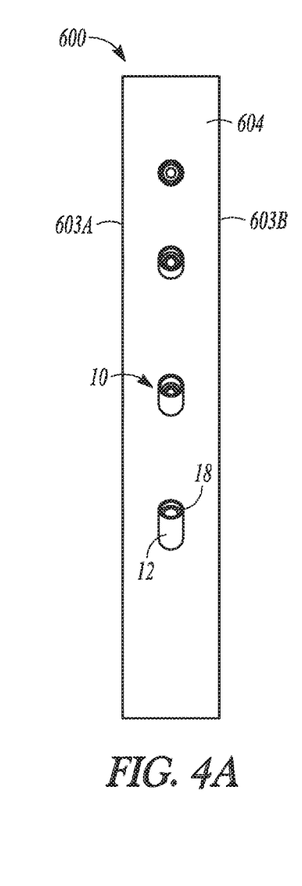
FIG. 4A is a top view of a model and a plurality of implant analogs, in accordance with another example of the present disclosure.
Figure 4B:
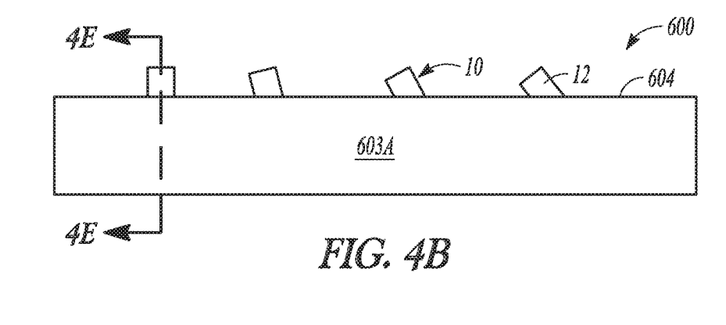
FIG. 4B is a first side view of the model and the plurality of implant analogs, in accordance with an example of the present disclosure.
Figure 4C:
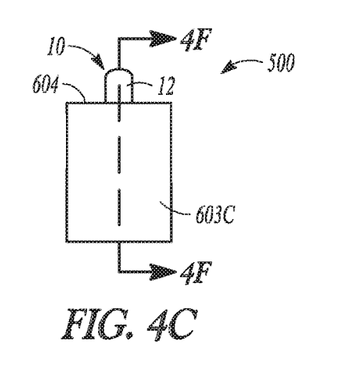
FIG. 4C is second end view of the model and the plurality of implant analogs, in accordance with an example of the present disclosure.
Figure 4D:
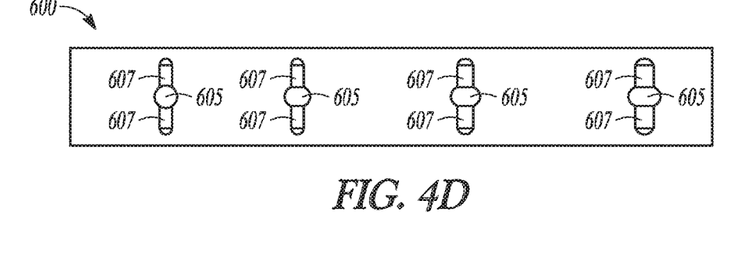
FIG. 4D is a bottom view of the model and the plurality of implant analogs, in accordance with an example of the present disclosure.
Figure 4E:
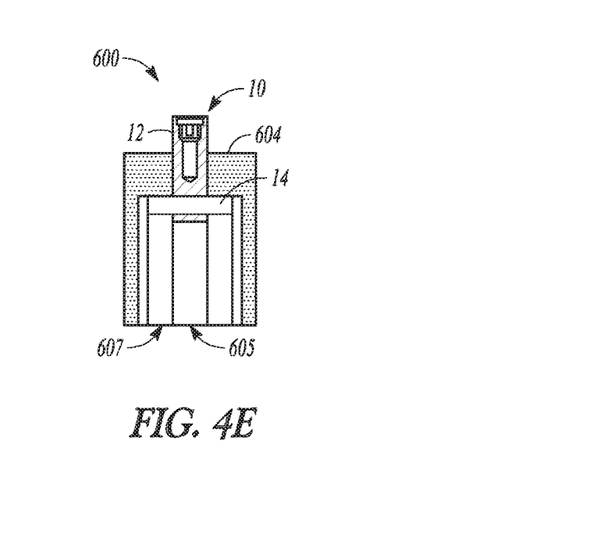
FIG. 4E is a cross-sectional view of the model taken through one of the implant analogs, the cross-section taken along line 4E-4E of FIG. 4B.
Figure 4F:
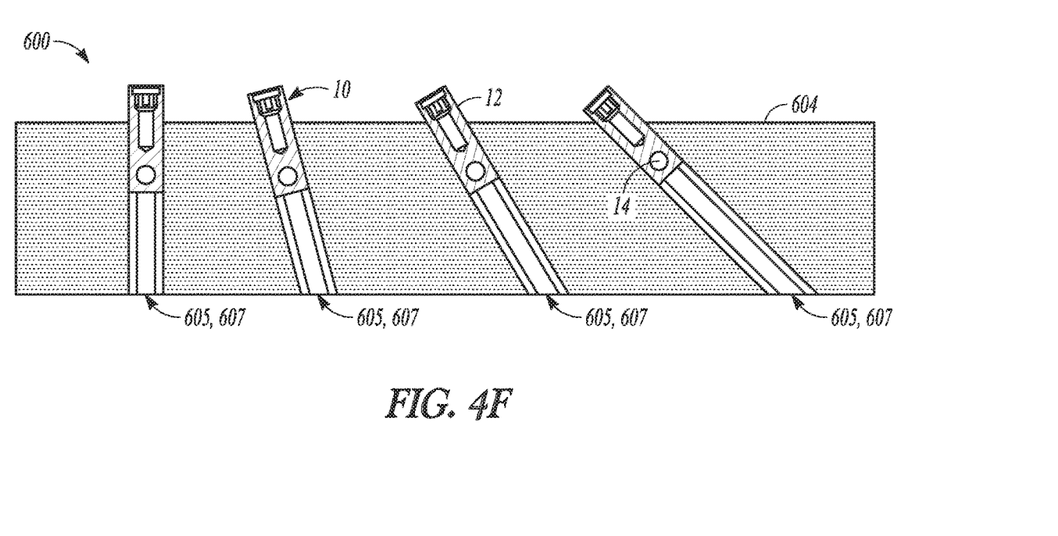
FIG. 4F is a second cross-sectional view of the model taken through one of the implant analogs, the cross-section taken along line 4F-4F of FIG. 4C.
Figure 5A:
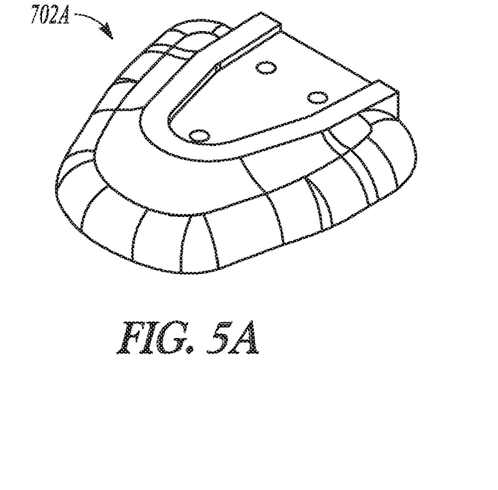
FIGS. 5A-5J are various views of a base in accordance with an example of the present disclosure.
Figure 5B:
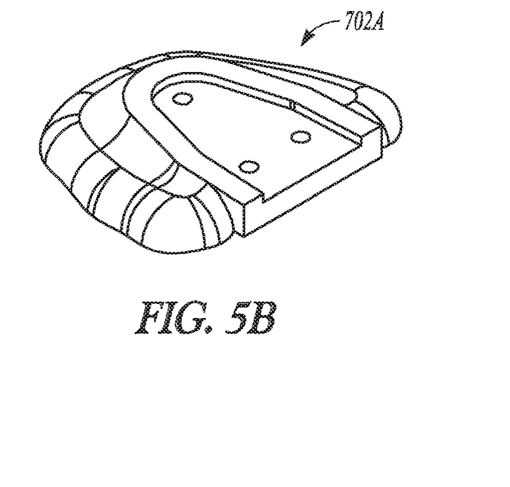
Figure 5C:
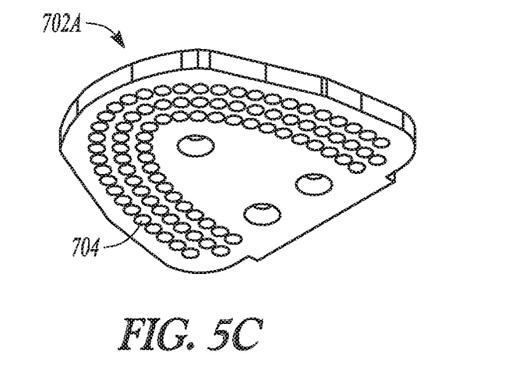
Figure 5D:
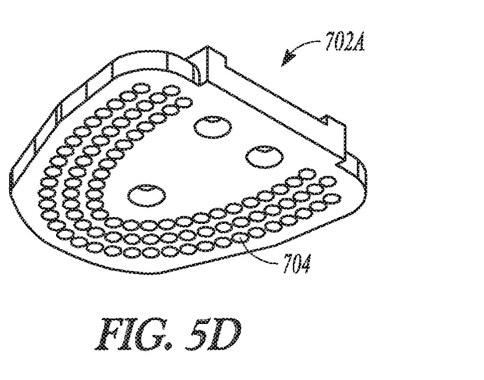
Figure 5E:
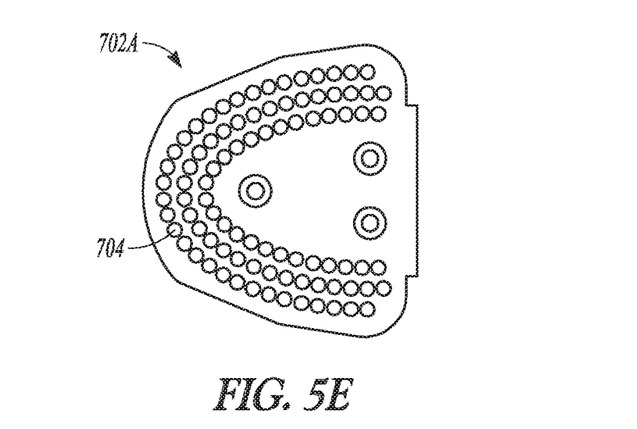
Figure 5F:
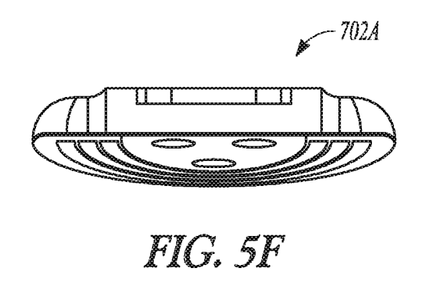
Figure 5G:
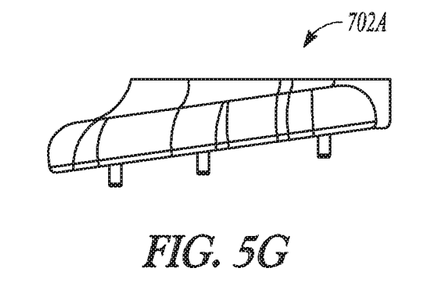
Figure 5H:
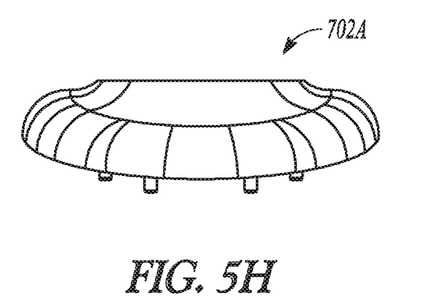
Figure 5I:
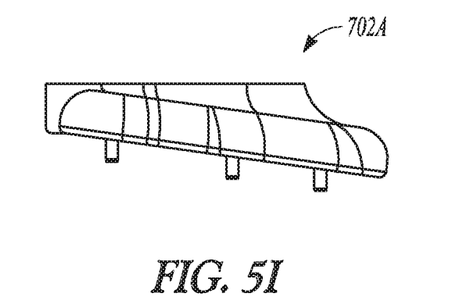
Figure 5J:
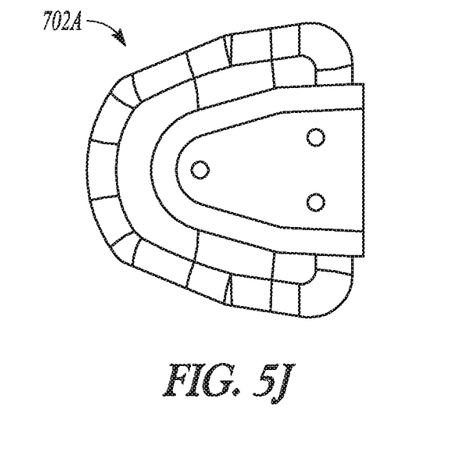
Figure 6A:
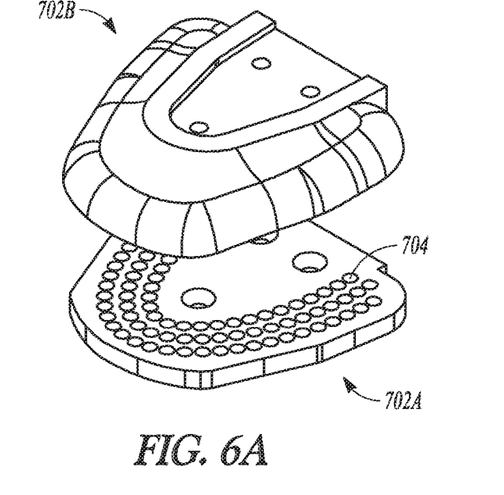
FIGS. 6A-6H are various views of the base of FIGS. 5A-5J in conjunction with a second base and various positioning elements.
Figure 6B:
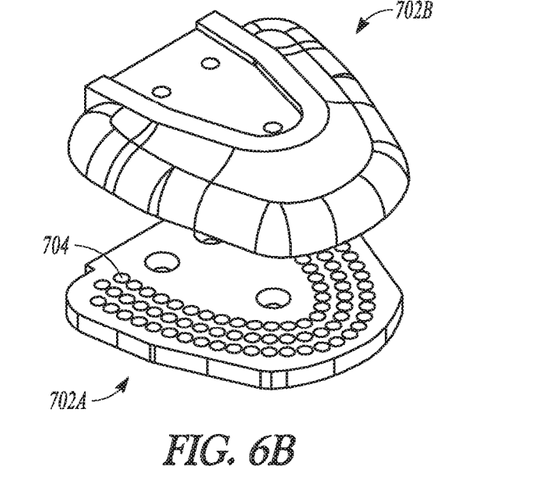
Figure 6C:
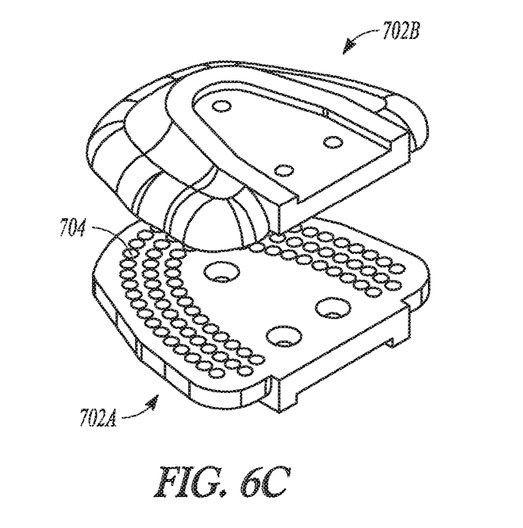
Figure 6D:
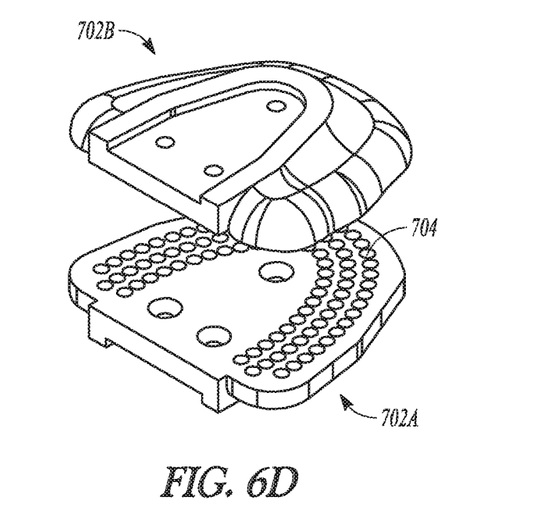
Figure 6E:
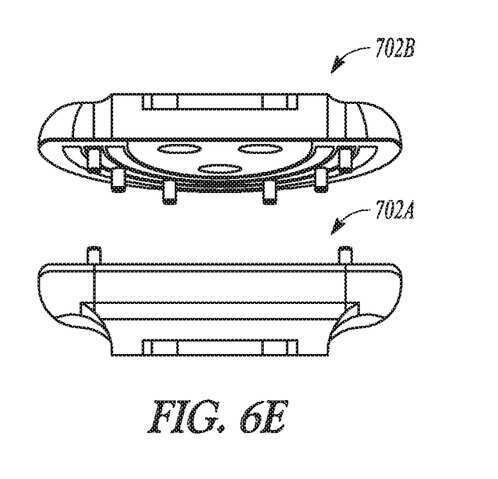
Figure 6F:
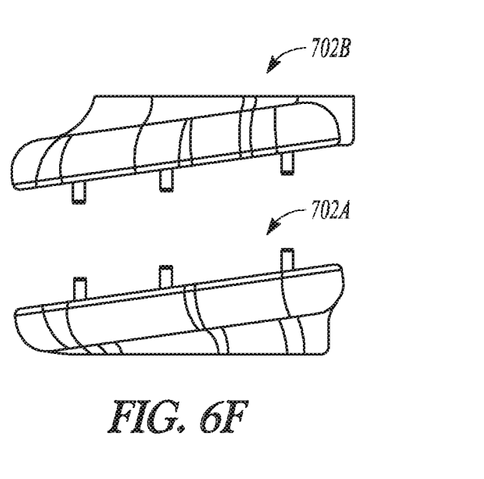
Figure 6G:
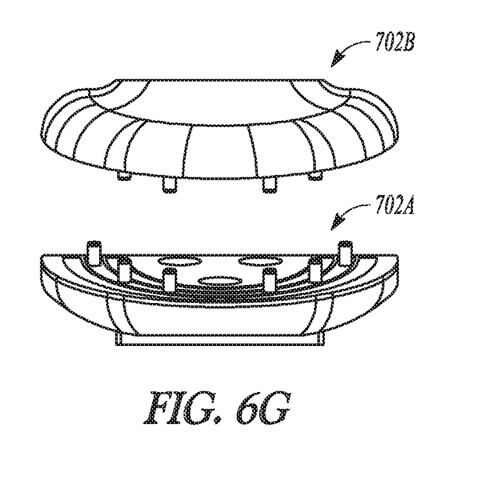
Figure 6H:
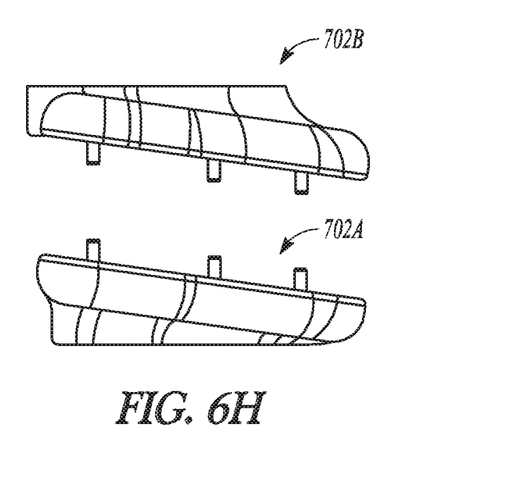
Figure 7A:
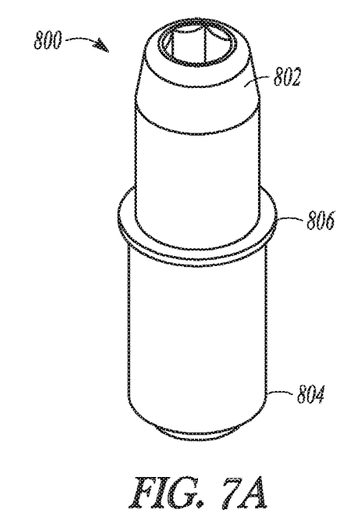
FIGS. 7A-7D are various views of positioning element, in accordance with an example of the present disclosure.
Figure 7B:
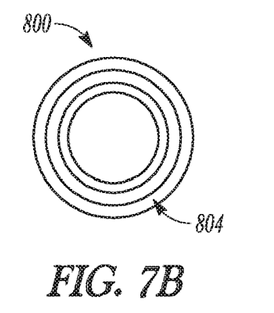
Figure 7C:
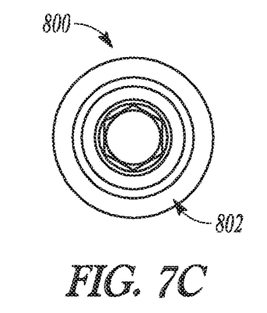
Figure 7D:
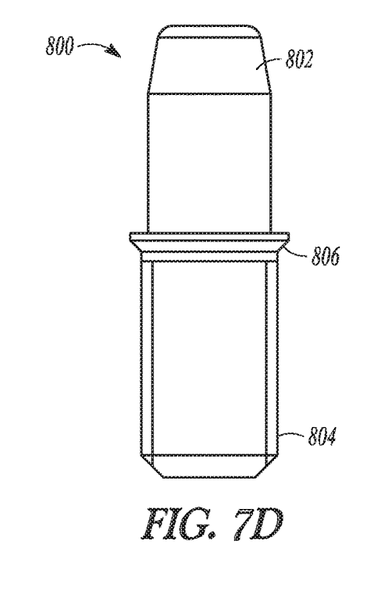

FIGS. 4A-4F illustrate a highly schematic example of a model 600, according to another disclosed example. Although described in reference to a model, in some instances, a bridge or separate component that can be removed from inserted in a model can also be used in a manner similar to as described as follows. FIGS. 4A, 4B, 4C, and 4D provide plan views of the model 600 from various sides including the top, first side, second side, and bottom. FIGS. 4E and 4F are cross-sections of the implant analog taken along lines indicated in FIGS. 4B and 4C. As illustrated in FIGS. 4D-4F, the model 600 can include a plurality of primary bores 605 therein. The model 600 can additionally include a plurality of transverse bores 607 (FIG. 4D).

As illustrated in FIGS. 4A-4F the model 600 can receive one or more implant analogs 10 therein. As shown in FIG. 4A, the main body 12 of each implant analog 10 can extend from the primary bore to be positioned at least partially outside a working surface 604 of the model 600. This arrangement can allow the coronal portion 20 to receive (or potentially receive) a component that simulates an abutment or other type of dental implant feature. However, as illustrated in FIG. 4E, the model 600 can be configured such that each transverse component 14 is received in the corresponding transverse bore 607. As will be understood, in some instances each transverse bore 607 can include features such as tapered walls, detents, tabs, etc. that allow for affixation and retention of the corresponding transverse component 14, and thus, the implant analog 10 within the model 600. In other cases the addition of a component or head to the implant analog 10 can be used to affix the implant analog 10 by contacting working surface 604 and forcing the transverse component 14 into contact with a top wall of the transverse bore 607.

FIGS. 4B and 4C illustrate the model 600 from sides 603B and 603C, respectively. FIG. 4D illustrates the bottom base interfacing portion of the model 600. Attachment features that would allow the model 600 to mount to a base (not shown) are not illustrated in the highly schematic depiction of FIG. 4D. FIG. 4D and FIG. 4F illustrate that the primary bores 605 and transverse bores 607 can be angled relative to the working surface 604 (FIGS. 4A, 4B, 4C, 4E, and 4F). Thus, the primary bores 605 and secondary bore 607 may be angled relative to one another in some instances. The nature of the angle can be determined based upon various factors including size constraints of the component installed along the working surface of the model.

As discussed, the model 600 can be configured to receive the implant analogs 10 therein. The main body 12 of each implant analog 10 is affixed to the model 600 by the transverse component 14. The configuration of the model 600 and the implant analogs 10 can allow the process of positioning, affixing, and/or adjusting the implant analogs 10 within the model 600 to be simplified. In particular, the transverse component 14 can simply be grasped and/or pulled with or without tools to remove the transverse component 14 from the model 600. In other instances, the main body 12 may simply be pushed to back the main body out along primary bore 605 (and back transverse component 14 along transverse bore 607). This then allows the main body 12 to be adjusted or removed from the model 600 as necessary. Additionally, as each of the transverse passages within the model 600 has a fixed relationship relative to the implant analogs and other portions of the model 600 (e.g., working surface 604), the arrangement allows for alignment of the implant analog in a desired position in addition to affixation.

It should be noted that the base, models, implant analogs, and position defining elements described and subsequently described herein can comprise part of a digital model system. As previously discussed, the implant analogs can be configured with the transverse components to allow for precise positioning within the model and system. Additionally, the base can serve as the basis for accommodating various models. In some instances, the models and/or base can be produced by additive or subtractive manufacturing processes.

FIGS. 5A-5J and FIGS. 6A-6H provide views of a base 702A (and base 702B in FIGS. 6A-6H) from various perspectives according to an example of the disclosure. As illustrated in FIGS. 5C-5E and 6A-6D, the base 702 can have a plurality of holes 704 therein. The holes 704 are adapted to receive positioning elements (FIGS. 6A-6H and FIGS. 7A-7D) therein. The holes 704 are variously placed in the base 702A (and 702B) such that different models can be accommodated. In particular, secure placement of the model can be achieved with positioning elements. The various holes allow the placement of the positioning elements to be adjusted such that positioning elements that would interfere with implant analogs can be moved or removed. Additionally, the desired stability of the model can be adjusted by introducing or removing positioning elements. In some instances, the base, implant analogs, and/or positioning elements can be saved in a digital form (or example in CAD based design software) such that the model can be created virtually before physical production. In some instances, the base can be installed (e.g., cast) without the use of assistive devices with suitable adapters in various articulators.

FIGS. 7A-7D illustrate one example of a positioning element 800. The positioning element can have a coronal portion 802, an apical portion 804, and a shoulder 806 therebetween. The apical portion 804 is adapted to be received in holes (e.g., holes 704 in base 702) in a base. The shoulder 806 is adapted to seat against a surface of the base to allow the positioning element to have a desired depth. Coronal portion 802 can be adapted to be received in a model or an intermediary component has desired. Both the coronal portion 802 and the apical portion 804 can be provided with attachment features to allow for ease of installation or removal or for other purposes.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other examples can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A system for simulating a mouth of a patient, comprising:

first and second implant analogs each having a main body, a solid body portion, a bore through the solid body portion, and a component configured to extend transverse to the main body when received in the bore; and a model having first and second primary passages with the first primary passage having first and second transverse passages associated therewith and the second primary passage having third and fourth transverse passages associated therewith, wherein the first transverse passage extends transverse to the first primary passage, the second transverse passage extends transverse to the first primary passage, the third transverse passage extends transverse to the second primary passage and the fourth transverse passage extends transverse to the second primary passage, wherein the first and second primary passages extend entirely through the model and each has a first opening to a first coronal side of the model and a second opening to an opposing second apical side of the model, and wherein the first, second, third and fourth transverse passages each have a corresponding opening only to the apical side of the model that communicates with the second opening, wherein the first primary passage, the first transverse passage and the second transverse passage communicate such that the first implant analog is assembled outside the model with the component received in the bore and the assembled first implant analog is configured to be inserted through the second opening and the corresponding opening and into collectively the first primary passage, the first transverse passage and the second transverse passage, wherein the model is configured for the first primary passage to receive the main body of the first implant analog and for the first opening to allow a portion of the main body to extend from the first opening and protrude from the first side, and the first transverse passage and the second transverse passage in combination are configured to receive portions of the component when assembled to the main body, wherein the second primary passage, the third transverse passage and the fourth transverse passage communicate such that the second implant analog is assembled outside the model with the component received in the bore and the assembled second implant analog is configured to be inserted through the second opening and the corresponding opening and into collectively the second primary passage, the third transverse passage and the fourth transverse passage, wherein the model is configured for the second primary passage to receive the main body of the second implant analog and for the first opening to allow a portion of the main body to extend from the first opening and protrude from the first side, and the third transverse passage and the fourth transverse passage in combination are configured to receive portions of the component when assembled to the main body, and wherein the first and second transverse passages include one or more fixation or retention mechanisms configured to contact and affix the component of the first implant analog to the model with the main body protruding from the first side, and the third and fourth transverse passages include one or more fixation or retention mechanisms configured to contact and affix the component of the second implant analog relative to the model with the main body protruding from the first side.

2. The system of claim 1, further comprising:
a base having a primary surface and a plurality of holes therein, the holes opening along the primary surface; and
one or more positioning elements having an apical portion adapted to be received in at least one of the holes, wherein the positioning elements have a coronal portion adapted to be received in the model.

3. The system of claim 1, wherein the first and second implant analogs each has a different sized main body.

4. The system of claim 1, wherein the model is configured to represent an accurate model of the patient's jaw.

5. The system of claim 1, wherein the model includes a working surface that is configured to receive one or more components that simulate abutments or other dental implant components.

6. The system of claim 1, wherein the bore through the solid body portion of each of the first and second implant analogs comprises an entry opening on a first side of the solid body and an exit opening on a second side of the solid body, the entry and exit openings being tapered.

7. The system of claim 1, wherein the first and second implant analogs each has a coronal end with an attachment member configured to receive a second component that simulates a dental implant, and the attachment member and the bore through the solid body portion do not intersect within the solid body portion.

8. The system of claim 1, wherein the one or more fixation or retention mechanisms comprise the first, second, third and fourth transverse passages having tapered walls, detents, or tabs configured to contact and affix the components of the first and second implant analogs, respectively, relative to the model.

9. The system of claim 1, wherein the second side comprises a non-model side of the model, and wherein the first side comprises an anatomical side of the model.

10. The system of claim 1, wherein the first primary passage is angled relative to the second primary passage.

11. A method for affixing an implant analog to a model, comprising:
assembling a first component with a first main body to form a first implant analog by inserting the first component into a receptacle in the first main body, wherein the first implant analog is assembled external to the model;
assembling a second component with a second main body to form a second implant analog by inserting the second component into a receptacle of the second main body, wherein the second implant analog is assembled external to the model;
passing the assembled first implant analog through the model via insertion through a first opening at an apical side of the model and via a first primary passage configured to receive the first main body and a first transverse passage configured to receive the first component;
passing the assembled second implant analog through the model via insertion through a second opening at the apical side of the model and via a second primary passage configured to receive the second main body and a second transverse passage configured to receive the second component, wherein the first and second transverse passages intersect and are transverse, respectively, to the first primary passage and the second primary passage, wherein the first and second primary passages extend entirely through the model from the apical side to an opposing coronal side, and wherein the model has third openings at the coronal side configured to allow a portion of the main body extend therethrough and to protrude from the coronal side; and
affixing the first and second components within the first and second transverse passages, respectively, thereby coupling the first and second implant analogs to the model with the main body protruding from the coronal side.

12. The method of claim 11, wherein each of the first and second implant analogs has a coronal end with an attachment member configured to receive the second component that simulates a dental implant, and the attachment member and a bore are spaced from one another and do not intersect with one another within the first or second body.

13. The method of claim 11, wherein the receptacle of the first implant analog comprises an entry opening on a first side of the main body and an exit opening on a second side of the main body, the entry and exit openings being tapered.

14. The method of claim 11, wherein the first and second transverse passages comprise one or more fixation or retention mechanisms, and the method further comprises contacting the first and second components with the one or more fixation or retention mechanism within the first and second transverse passages to affix the first and second components relative to the model, respectively, using the fixation or retention mechanisms.

15. The method of claim 14, wherein the one or more fixation or retention mechanisms comprise the first and second transverse passages having tapered walls, detents, or tabs configured to contact and affix the first and second components, respectively, relative to the model.

16. The method of claim 11, wherein the first primary passage is angled relative to the second primary passage.

\* \* \* \* \*